US010858674B2

(12) United States Patent
Sarks et al.

(10) Patent No.: US 10,858,674 B2
(45) Date of Patent: Dec. 8, 2020

(54) METHODS AND SYSTEMS FOR PROPAGATING MICROORGANISMS ON STILLAGE COMPOSITIONS (71) Applicant: POET Research, Inc., Sioux Falls, SD (US)

(72) Inventors: Cory J. Sarks, Sioux Falls, SD (US); Rodney Duane Pierson, Wentworth, SD (US); Malgorzata M. Slupska, Sioux Falls, SD (US)

(73) Assignee: POET Research, Inc., Sioux Falls, SD (US)

( * ) Notice: Subject to any disclaimer, the term of this patent is extended or adjusted under 35 U.S.C. 154(b) by 0 days.

(21) Appl. No.: 16/220,993

(22) Filed: Dec. 14, 2018

(65) Prior Publication Data
US 2019/0185886 A1  Jun. 20, 2019

Related U.S. Application Data (60) Provisional application No. 62/598,717, filed on Dec. 14, 2017.

(51) Int. Cl.
C12P 7/10 (2006.01)
C12P 7/08 (2006.01)
C12P 19/04 (2006.01)
C12P 1/02 (2006.01)
C12P 7/06 (2006.01)
C12P 19/02 (2006.01)
C12N 9/26 (2006.01)
C12N 9/42 (2006.01)
C12R 1/865 (2006.01)

(52) U.S. Cl.
CPC .............. C12P 7/10 (2013.01); C12N 9/2411 (2013.01); C12N 9/2437 (2013.01); C12P 1/02 (2013.01); C12P 7/06 (2013.01); C12P 7/08 (2013.01); C12P 19/02 (2013.01); C12P 19/04 (2013.01); C12R 1/865 (2013.01); C12Y 302/01001 (2013.01); C12Y 302/01004 (2013.01)

(58) Field of Classification Search
None
See application file for complete search history.

(56) References Cited

U.S. PATENT DOCUMENTS

| | | | |
|---|---|---|---|
| 4,530,846 A | 7/1985 | Nagodawithana et al. | |
| 5,424,417 A | 6/1995 | Torget et al. | |
| 6,022,419 A | 2/2000 | Torget et al. | |
| 6,159,724 A | 12/2000 | Ehret | |
| 7,344,876 B2 | 3/2008 | Levine | |
| 7,622,284 B2 | 11/2009 | Op Den Camp et al. | |
| 7,820,418 B2 | 10/2010 | Karl et al. | |
| 7,842,484 B2 | 11/2010 | Lewis | |
| 7,919,291 B2 | 4/2011 | Lewis et al. | |
| 7,968,320 B2 | 6/2011 | Degre et al. | |
| 8,105,801 B2 | 1/2012 | Nielsen et al. | |
| 8,450,094 B1 | 5/2013 | Narendranath et al. | |
| 8,603,801 B1 * | 12/2013 | Dale ........................ | C11B 13/00 435/271 |
| 8,815,552 B2 | 8/2014 | Narendranath et al. | |
| 9,034,631 B2 | 5/2015 | Narendranath et al. | |
| 9,234,167 B2 | 1/2016 | Narendranath et al. | |
| 9,340,767 B2 | 5/2016 | Narendranath | |
| 9,416,376 B2 | 8/2016 | Narendranath et al. | |
| 9,540,664 B2 | 1/2017 | Lewis et al. | |
| 10,190,086 B2 | 1/2019 | Narendranath et al. | |
| 2004/0058429 A1 | 3/2004 | Bill et al. | |
| 2004/0234649 A1 | 11/2004 | Lewis et al. | |
| 2006/0051847 A1 | 3/2006 | Gunnarsson et al. | |
| 2006/0246563 A1 | 11/2006 | Eroma et al. | |
| 2009/0093027 A1 | 4/2009 | Balan et al. | |
| 2009/0325241 A1 | 12/2009 | Jeffries et al. | |
| 2010/0124759 A1 | 5/2010 | Wang et al. | |
| 2010/0159552 A1 | 6/2010 | Benson et al. | |
| 2010/0196994 A1 | 8/2010 | van Leeuwen et al. | |
| 2010/0227369 A1 | 9/2010 | Narendranath et al. | |
| 2011/0262983 A1 | 10/2011 | Jeffries et al. | |
| 2011/0269202 A1 | 11/2011 | Taron et al. | |
| 2012/0309069 A1 | 12/2012 | Bell et al. | |
| 2014/0065700 A1 | 3/2014 | Narendranath et al. | |
| 2014/0273166 A1 | 9/2014 | Narendranath | |
| 2014/0273167 A1 | 9/2014 | Narendranath et al. | |
| 2015/0072390 A1 | 3/2015 | Narendranath et al. | |
| 2018/0171285 A1 | 6/2018 | Narendranath et al. | |
| 2019/0002940 A1 | 1/2019 | Karl | |
| 2019/0071696 A1 | 3/2019 | Sarks et al. | |

(Continued)

FOREIGN PATENT DOCUMENTS

WO   WO 2011/159915   12/2011
WO   WO 2012/100187   7/2012

(Continued)

OTHER PUBLICATIONS

Valdivia et al. (2016) "Biofuels 2020: Biorefineries based on lignocellulosic materials", Microbial Biotechnology, 9:585-594.

(Continued)

Primary Examiner — Heidi Reese
(74) Attorney, Agent, or Firm — Kagan Binder, PLLC (57) ABSTRACT Provided are methods and systems of propagating a microorganism on a stillage composition. The methods involve growing microorganisms in a propagation medium formed from a polysaccharide-containing stillage composition with the majority of the of the polysaccharides in the propagation medium coming from the stillage composition. The propagation medium also includes cellulases and/or amylases to form monosaccharides from the polysaccharides. A first cell mass is grown in the propagation medium to form a second cell mass which is greater than the first cell mass.

20 Claims, 4 Drawing Sheets (56) References Cited

U.S. PATENT DOCUMENTS

| | | |
|---|---|---|
| 2019/0112568 A1 | 4/2019 | Narendranath et al. |
| 2019/0144816 A1 | 5/2019 | Sarks et al. |
| 2019/0256873 A1 | 8/2019 | Sarks et al. |
| 2019/0292573 A1 | 9/2019 | Carlson et al. |

FOREIGN PATENT DOCUMENTS

| | | |
|---|---|---|
| WO | 2012103281 A2 | 8/2012 |
| WO | WO 2012/125739 | 9/2012 |
| WO | 2014/159529 A1 | 10/2014 |
| WO | 2014/160184 A1 | 10/2014 |
| WO | 2016/205596 A1 | 12/2016 |
| WO | 2017/218380 A1 | 12/2017 |

OTHER PUBLICATIONS

Zhang et al. (2019) "Effect of diluted hydrolysate as yeast propagation medium on ethanol production", Bioresource Technology, 271:1-8.

Jeffries, T.W. et al., (1988) "Fermentation of Hemicellulosic Sugars and Sugar Mixtures by *Candida shehatae*", Biotechnology and Bioengineering, 31:502-506.

Aiba et al., (1976) "Fed batch culture of *Saccharomyces cerevisiae*: a perspective of computer control to enhance the productivity in baker's yeast cultivation", Biotechnology and Bioengineering, 28: 1001-1016.

Soni et al., (2003) "A solid state fermentation based bacterial alpha-amylase and fungal glucoamylase system and its suitability for the hydrolysis of wheat starch", Process Biochemistry, VOi, 39:185-192.

Kurth. E.F., (1946) "Yeasts from Wood Sugar Stillage", Industrial and Engineering Chemistry, 38(2):204-207.

\* cited by examiner

ABSTRACT# METHODS AND SYSTEMS FOR PROPAGATING MICROORGANISMS ON STILLAGE COMPOSITIONS

BACKGROUND

Propagating microorganisms, namely to increase the quantity of the microorganisms, may be desirable for one or more reasons. For example, it may be desirable when a particular microorganism is expensive or when a microorganism can be used as feed or feed supplements.

Also desirable is the ability to use alternative, more accessible, or more economical components in a propagation medium (e.g., lignocellulosic material, and the like). However, the hydrolysis or break down of lignocellulosic materials can produce one or more by-products that can inhibit activity of enzymes, growth of yeast and other microorganisms, and/or fermentation of monosaccharides to a biochemical.

There is a continuing need to provide compositions, methods, and systems to propagate microorganisms, particularly for fermentation.

SUMMARY

The current invention is directed to methods, compositions, and systems that use a stillage composition for propagating a microorganism in a propagation medium. Stillage compositions such as whole stillage or syrup can be used with amylolytic and/or cellulolytic enzymes to generate monomeric sugars sufficient for microorganism propagation, without the need for supplementing the propagation medium with other starch sources. Propagation can be carried out to generate significant increases in microorganism cell mass, and the cell mass is then used in a lignocellulosic fermentation processes.

As a general matter, the propagation method can be used after an industrial starch-based fermentation process which generates a stillage product, and before a lignocellulosic fermentation. Accordingly, the propagation method occurs between two different types of industrial fermentation processes. For example, a starch-based fermentation from corn can be carried out, providing a stillage composition, and the stillage composition is then used for the propagation method. Microorganism cell mass generated from the propagation method can then be used for a subsequent lignocellulosic fermentation process.

In an embodiment, the invention provides a method of propagating a microorganism to generate a cell mass that is used in a subsequent lignocellulosic fermentation process. The method includes providing a propagation medium formed from a stillage composition including polysaccharides. The stillage composition is obtained from a starch based fermentation process. The majority of the polysaccharides in the propagation medium are from the stillage composition. The propagation medium also includes an enzyme component comprising one or more cellulases, amylases, or combinations thereof, which can convert the polysaccharides into one or more monosaccharides by enzymatic action. During the method, a first cell mass of the microorganism is grown in the propagation medium with monosaccharides to form a second cell mass that is greater than the first cell mass. The second cell mass is then used in a lignocellulosic fermentation process.

In some modes of practice, the generation of monosaccharides and microorganism growth happen simultaneously, and this mode of practice can provide additional advantages for generating cell mass. During the cell growth, the propagation medium can be oxygenated to promote growth of the microorganism over bioproduct formation, which is different than fermentation where anaerobic conditions generally amplify bioproduct formation at the expense of cell growth.

In another embodiment, the invention provides a propagation medium consisting essentially of (i) a stillage composition that is whole stillage or syrup, (ii) one or more cellulases, amylases and/or combinations thereof that can convert the stillage composition into one or more monosaccharides, and a first cell mass of a microorganism, and optionally (iii) water.

In another embodiment, the invention provides a method for obtaining a stillage composition, using the stillage composition to propagate a microorganism, and then performing lignocellulosic fermentation. The method includes obtaining a stillage composition from a starch-based fermentation process that uses a plant material, wherein the stillage composition includes polysaccharides. A propagation medium is formed for propagating a microorganism, the medium including the stillage composition from the starch-based fermentation process, wherein polysaccharides in the propagation medium consist essentially of the polysaccharides from the stillage composition. The propagation medium also includes an enzyme component comprising one or more enzymes selected from cellulases, amylases, and combinations thereof. The polysaccharides are converted into one or more monosaccharides using the enzyme component, and the microorganism is propagated in the propagation medium to generate a cell mass. The cell mass is then used in a lignocellulosic fermentation process.

Methods, compositions, and systems of the disclosure provide advantages for generating cell mass, such as significant quantities of yeast that can subsequently be used in a lignocellulosic fermentation process. For example, stillage compositions can be obtained from non-cellulosic (e.g., corn) fermentation processes and used to form propagation mediums without supplementing the propagation medium with other starch sources, such as those used for preparing fermentation medium, or using supplemental nutrients. Further, methods of the disclosure can avoid use of cellulosic feedstocks which can otherwise be detrimental to cell growth.

DETAILED DESCRIPTION

As used herein, the term "ethanologen" refers to a microorganism that can convert one or more monosaccharides (e.g., glucose and the like) into at least ethanol.

As used herein the term "saccharification" refers to the production of fermentable sugars from polysaccharides particularly through the use of enzymes.

As used herein the term "fermentation" refers broadly to the breakdown of organic substances by microorganisms to produce fermentation products. Fermentation generally occurs under conditions using no, or limited amounts of, oxygen and which promote significant bioproduct formation at the expense of cell growth.

As used herein the term "propagation" refers to reproducing an initial (e.g. starter) population of microorganisms to generate a cell population larger than the initial population. As such, propagation can be considered as converse to fermentation, wherein in propagation significant cell growth occurs at the expense of bioproduct formation.

As used herein the term "stillage composition" refers to the post distillation components obtained after fermentation. The stillage composition encompasses whole stillage, thin stillage, wet cake and/or syrup.

As used herein, the term "consisting essentially" means that there is no more than 1% (wt) of other, non-specified, components in a composition.

As used herein the term "propagation media" refers to a composition that is used to grow microorganisms of the disclosure, wherein the propagation media includes stillage composition and one or more enzymes active on one or more components of the stillage composition.

Disclosed are methods and systems for propagating microorganisms using a stillage composition. The stillage composition can be obtained from a backend of a fermentation process. Enzymes such as cellulases and amylases are added to the stillage composition to break down polysaccharides present in the stillage composition to release monosaccharides. The resultant monosaccharides in the stillage composition are used to propagate microorganisms.

A stillage composition can include components remaining after distillation or separation of a bioproduct (e.g., ethanol) in a fermentation media. For example, a stillage composition can be obtained after distillation of a fermentation medium, the fermentation medium obtained from a fermentation processes which can include steps of grinding sugar-containing materials (e.g., starch containing materials) in a dry-grind or wet-milling process, then breaking down or saccharifying the material into sugars using enzymes, and finally converting the sugars directly or indirectly into a desired product such as ethanol through fermentation using a fermenting microorganism. The fermentation product or beer can include ethanol, water, oil, additional soluble components, unfermented particulate matter, residual fibers and polysaccharides, and the like. The beer can then be distilled to provide ethanol, leaving the remaining components as "whole stillage."

In one embodiment, the stillage composition is obtained after distillation or separation of ethanol from a fermentation medium of an ethanol fermentation production process. In one embodiment, the stillage composition is obtained after ethanol fermentation using a process involving treatment of raw starch with glucoamylase and alpha amylase as disclosed in U.S. Pat. Nos. 7,842,484 and 7,919,291 that are each hereby incorporated by reference in their entireties.

Accordingly, propagation processes of the disclosure using stillage compositions can optionally be described including processing steps leading to the formation of a stillage composition. These optional "upstream" steps can include forming a fermentation medium from a plant material, fermenting a microorganism in the fermentation medium to make a bioproduct, distilling or purifying a bioproduct from the fermentation medium, and/or forming stillage composition from the distilled fermentation medium.

The source or plant materials used to make a fermentation medium, that then results in the stillage composition, includes various sources such as, for example, tubers, roots, stems, cobs, leaves, legumes, cereals, whole grain, or corn kernels. In one embodiment, starch can be used for fermentation, the starch being obtained from, for example, corn, cobs, wheat, barley, rye, milo, sago, cassava, tapioca, sorghum, rice, peas, bean, banana or potatoes.

The fermentation medium can be obtained by processes involving treatment of raw starch glucoamylase and alpha amylase as disclosed in U.S. Pat. Nos. 7,842,484 and 7,919,291 that are each hereby incorporated by reference in their entireties.

In one embodiment, the fermentation medium is prepared without creating a hot slurry (i.e., without cooking). In some embodiments, fermentation medium is prepared without a liquefaction step. The fermentation process may be carried out simultaneously with a saccharification step, simultaneous saccharification and fermentation (SSF), of a starch composition with an enzyme composition to form a saccharified composition (e.g., without cooking) that is simultaneously fermented. In some embodiments, the enzyme composition used for saccharification can include an alpha amylase and glucoamylase added at a pH in the range of about 3 to about 6, or at a pH in the range of about 4 to about 5. In some embodiments, the enzyme composition used for saccharification is added at a temperature in the range of about 25° C. to about 40° C. Fermentation may be performed using a yeast, e.g., from *Saccharomyces* spp.

In another embodiment, a fermentation medium for a fermentation process can be prepared by a conventional enzymatic liquefaction process. In embodiments, the starch slurry or cellulosic materials may be heated to a temperature in the range of about 50° C. to about 100° C. (i.e., cooked), about 60° C. to about 90° C., or about 80° C. to about 85° C. Next, a thermostable alpha-amylase can be added to initiate liquefaction.

The slurry for the fermentation medium can then be jet-cooked at a temperature in the range of about 100° C. to about 145° C. to complete gelatinization of the slurry or in the range of about 102° C. to about 135° C., or about 105° C. to about 125° C. to complete gelatinization of the slurry.

The slurry can be cooled to a temperature in the range of about 50° C. to about 100° C., about 65° C. to about 97° C., or about 60° C. to about 95° C. Next, an additional alpha-amylase can be added to finalize hydrolysis. The liquefaction process can be generally carried out at a pH of in the range of about 3 to about 8, about 4 to about 7, or about 5 to about 6.

In one embodiment of the conventional enzymatic liquefaction process for preparation of a fermentation medium, the dextrins from the liquefaction may be further hydrolyzed to produce low molecular sugars DP1-3 that can be metabolized by microorganisms (e.g. yeast). The hydrolysis may be typically accomplished using glucoamylases, alternatively or in addition to glucoamylases, alpha-glucosidases and/or alpha-amylases can be used. In some modes of practice, a full saccharification step can last up to 72 hours. In an embodiment, a pre-saccharification step lasting 40-90 minutes at a temperature above 50° C. can be followed by a complete saccharification via (SSF). In one embodiment of the conventional enzymatic liquefaction process, fermentation may be performed using a yeast, e.g., from *Saccharomyces* spp., which is added to the milled and liquefied whole grains (e.g., mash).

In one embodiment, raw material containing starch may be milled to open up the structure and allow for further processing. Dry milling as well as wet milling may be used. When wet milling is applied, the steps of soaking or steeping may precede milling. Both dry and wet milling is well known in the art of alcohol manufacturing.

Fermentation can be commenced by adding yeast to the fermentation medium and fermenting the yeast according to art known methods. Methods for producing alcohol during fermentation are disclosed in U.S. Pat. Nos. 7,842,484 and 7,919,291 and are hereby incorporated by reference in their entireties. The product of the fermentation process can be referred to as "beer," for example, fermenting corn produces "corn beer". Ethanol can be recovered from the fermentation mixture, from the beer, by any of a variety of known processes. For example, ethanol can be recovered by distillation. In one embodiment, the stillage composition is obtained after distillation or separation of ethanol from a beer or fermentation medium of an ethanol fermentation production process. The composition remaining after distillation of ethanol from the beer or fermentation media can be referred to as "whole stillage." Whole stillage can be further separated to provide a liquid component, referred to as "thin stillage" and a solid component, referred to as "wet cake" or "wet grains." The solid component can be dried to provide the "Distillers Dried Grains" (DDG). Thin stillage can be evaporated to provide condensate and "syrup" or may alternatively be recycled directly to a slurry tank as "backset." The syrup may be blended into DDG or added to the wet cake before drying to produce "Distillers Dried Grain with Solubles" (DDGS). Whole stillage, processed stillage forms (thin stillage, wet cake, DDG, syrup) as described herein, or combinations of any of these compositions can be used to form the propagation media.

Figure 1:
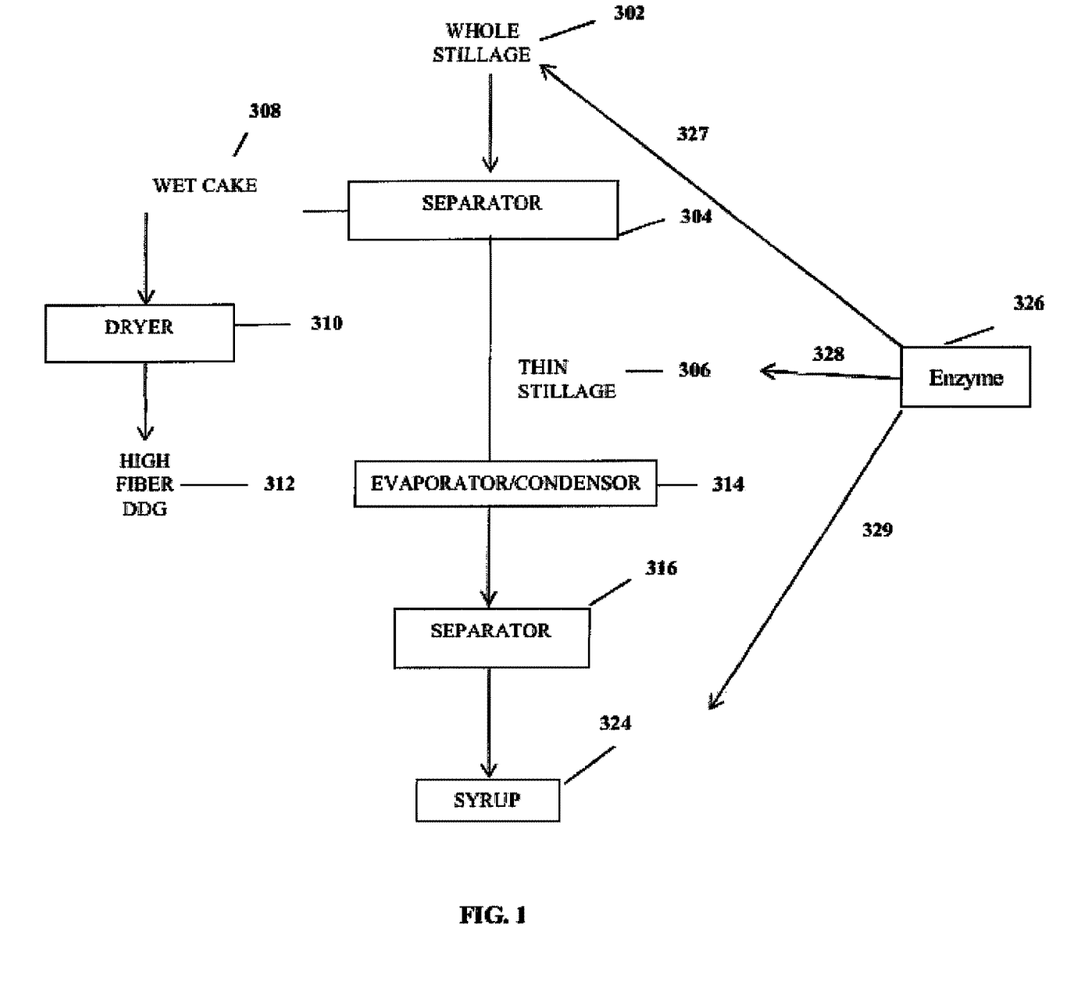
FIG. 1 is a schematic block diagram illustrating an embodiment of a system for fractionating whole stillage.

FIG. 1 is referenced to illustrate systems and methods that can be used to process stillage, which in turn can be used to form the propagation media. In an embodiment and shown in FIG. 1, is an example of a system for fractionation of the whole stillage. In this example, the whole stillage 302 is provided to a stillage separator 304 for separation of the stillage into a solids component and a liquid thin stillage 306. The separation may be performed through screw press, centrifugation, decanters, or via filtration type methodologies. In some embodiments, the separation may be performed utilizing a screen bowl centrifuge. One of ordinary skill in the art will appreciate that the speed or amount of centrifugal force applied will depend on various factors such as sample size and may be adjusted appropriately depending on such factors.

The solid component or wet cake 308 contains a high fiber cake, which may be dried at a dryer 310 to a high fiber dried distillers grain (DDG) 312 product. In some embodiments, the fiber cake may additionally undergo a washing step prior to being dried. In some embodiments, the wash fluid may be combined with the liquid thin stillage. Separation of the solid component from the thin stillage may be performed soon after initial production of the stillage.

The resulting liquid thin stillage 306 is provided to an evaporator 314 or a series of evaporators to condense the thin stillage to syrup 324. The whole stillage and/or the resultant products from the process depicted in FIG. 1, for example, thin stillage, wet cake and/or syrup can be used to make a propagation medium used for propagating microorganisms. One or more enzymes can be added at one or more points of processing and production of stillage composition to facilitate the further breakdown of polysaccharides and other sugars into monosaccharides such as glucose, xylose, or arabinose. As shown in FIG. 1, enzyme 326 may be added to the stillage composition at 327, 328 and 329. Alternatively, enzymes may be added to the stillage composition along with other components to form a propagation medium e.g. in a propagation vessel.

A whole stillage composition will generally have an amount of solids in the range of about 10% (wt) to about 30% (wt), about 10% (wt) to about 25% (wt), about 12% (wt) to about 20% (wt), about 12% (wt) to about 15% (wt), or about 15% (wt) to about 20% (wt). Of the solids in the composition, generally about 70% (wt) to about 80% (wt) are polysaccharides, and of those polysaccharides about 40% (wt) to about 50% (wt) are polysaccharides having repeating glucopyranose units that are joined by α-1,4 linkages such as starch, amylose, and maltodextrin. The remaining polysaccharides include those such as hemicellulose (a heteropolymer) and cellulose (a polysaccharide having repeating glucopyranose units that are joined by β-1,4 linkages) and are generally in the range of about 50% wt to about 60% wt of the solids components. Monomeric or dimeric sugars are typically at very low or undetectable amounts in the whole stillage composition, such as less than about 0.1% wt, or less than about 0.05% wt.

A syrup composition will generally have an amount of solids in the range of about 15% (wt) to about 40% (wt), about 20% (wt) to about 35% (wt), or about 25% (wt) to about 35% (wt). Of the solids in the syrup composition, generally about 50% (wt) to about 65% (wt) are polysaccharides, and of those polysaccharides about 40% (wt) to about 55% (wt) are polysaccharides such as starch, amylose, or maltodextrin. The remaining polysaccharides include those such as hemicellulose, cellulose are generally in the range of about 45% wt to about 60% wt of the solids components. Monomeric or dimeric sugars are typically at very low or undetectable amounts in the syrup stillage composition, such as less than about 0.1% wt, or less than about 0.05% wt.

A thin stillage composition will generally have an amount of solids in the range of about 3% (wt) to about 15% (wt), or about 6% (wt) to about 8% (wt), and can include starch, hemicellulose, and cellulose polysaccharides.

In one embodiment, the stillage composition is about 40% by volume or greater of the propagation medium, 50% by volume or greater of the propagation medium, such as in the range of about 75% to 100% by volume, or about 95 to 100% by volume, of the propagation medium. In still other embodiments, the propagation medium consists of 95-100% by volume stillage composition, and one or more enzymes. In some embodiments, the propagation medium includes 95-100% by volume stillage composition and is not supplemented with nitrogen sources, or sugar sources such as glucose or xylose or both.

The majority (i.e., greater than 50% (wt)) of the polysaccharides in the propagation medium are from the stillage composition. In preferred embodiments, at least 95% (wt) of the polysaccharides in the propagation medium are from the stillage composition. More specifically, and in embodiments, 96% (wt) or greater, 97% (wt) or greater, 98% (wt) or greater, 99% (wt) or greater, 99.5% (wt) or greater, or 100% of the polysaccharides in the propagation medium are from the stillage composition. As used herein, when the polysaccharides in the propagation medium "consist essentially" of the polysaccharides from the stillage composition, it means that 99% (wt) or greater, of the polysaccharides in the propagation medium are from the stillage composition.

Using a stillage composition, such as whole stillage or syrup, a propagation medium can be described in terms of the amount of glucose polymer that is derived from the stillage composition. In embodiments the propagation medium includes an amount of starch and starch-derived polysaccharides (e.g., amylose, maltodextrin) in the range of about 2% (wt) to about 10% (wt), about 2.5% (wt) to about 10% (wt), about 3% (wt) to about 10% (wt), about 3% (wt) to about 9% (wt), about 3.5% (wt) to about 9.5% (wt), about 3.5% (wt) to about 9% (wt), about 4% (wt) to about 9% (wt), about 4% (wt) to about 8.5% (wt), or about 5% (wt) to about 9% (wt).

One or more enzymes are added to the stillage composition or propagation medium made therefrom to break down residual polysaccharides into monosaccharides such as glucose, xylose or arabinose. The monosaccharides are then used for growth or propagation of the microorganism. In embodiments, one or more enzymes include one or more cellulases or one or more amylases or combinations thereof. In embodiments, the enzymes (e.g. cellulase or amylase or both) are added to the whole stillage, thin stillage, syrup or combinations thereof, or propagation medium made therefrom. In some embodiments, amylases include alpha amylase, gluco-amylase and combinations thereof that are capable of breaking down starch to sugars. In embodiments, cellulases include one or more cellulases and hemicellulases that are capable of breaking down cellulose, hemicellulose to sugars.

The enzymes are added to the stillage composition or propagation medium made therefrom at about 0.001% w/w to 1% w/w of the solids content of the stillage composition. In other embodiments, the enzymes are added from 0.002 to 0.04% w/w, or 0.05 to 0.09% w/w of solids content of the stillage composition or propagation medium made therefrom. About 50% (wt) of polysaccharides are converted to monosaccharides when amylase is present at 0.07% w/w of the solids of the stillage composition/propagation medium at a temperature of about 55° C.

In embodiments, the enzymes used for breaking down the sugars in a saccharification step are a low pH, thermostable enzyme. In some embodiments, the enzymes are added to the stillage composition or propagation medium made therefrom at a pH less than 6.0. In other embodiments, the enzymes may be added to a stillage composition or propagation medium made therefrom at a pH less than 4.0, or at a pH from about 3-6, from 4-5 or 3-4. The enzymes may be added to the stillage composition or propagation medium made therefrom at temperatures from 50-90° C., from 75-90° C., or 50-80° C. In embodiments, saccharification occurs from about 1-24 hours, from 1-3 hours, 3-10 hours, 12-24 hours, 24-36 hours, or 36-48 hours. In embodiments, saccharification is for 24 hours at 50° C. to 80° C. before yeast addition or at the time of yeast addition.

In still other embodiments, the enzymes are added to the stillage composition or propagation medium made therefrom at a pH of less than 4.2 and at a temperature of 50 to 80° C. for 24 hours.

In embodiments, monosaccharides present in propagation medium after saccharification or breakdown of the polysaccharides in the stillage composition is in the range of about 0.1% (wt) to about 9% (wt), about 0.1% (wt) to about 5% (wt), about 0.1% (wt) to about 3.0% (wt)t about 0.1% (wt)t to about 2.0% (wt)t; from 0.1% (wt)t to 1.5% (wt)t; from 0.2% (wt)t to 1.5% (wt)t, from 0.5% (wt)t to 1.5% (wt)t, or 0.5-3.0% (wt)t of the propagation medium. These ranges can represent the amount of monosaccharides after saccharification or breakdown of the polysaccharides, but prior to consumption of the monosaccharides by microorganisms. During a simultaneous saccharification and propagation, the amount of monosaccharides can be at, or below, the minimum amounts of any of the ranges described herein, representing consumption of the monosaccharides during growth of the microorganisms.

Examples of commercially available amylase enzymes include FUELZYME™ (Verenium Corp, part of BASF), LpHERA™, LIQUOZYME™ (Novozymes); and gluco-amylase enzymes include SPIRIZYME™ (Novozymes).

Optional additional agents for propagating microorganisms such as yeast are well known and include antibiotics, supplemental or accessory enzymes, materials for adjusting and maintaining pH, and vitamins.

The resultant monosaccharides that result from saccharification of stillage composition or propagation medium made therefrom are used to grow or propagate microorganisms. In embodiments, microorganisms that are propagated are microorganisms that can convert one or more monosaccharides into a biochemical or fermentation product. Such microorganisms are well-known and include, e.g., bacteria and/or fungi such as yeast. The biochemical can vary depending on the conditions that are provided. In many embodiments, the biochemical includes biofuels such as ethanol, butanol, and the like. In some embodiments, the microorganism propagated includes one or more ethanologens.

The microorganism to be propagated and later used for fermentation include prokaryotic (e.g. bacteria) and eukaryotic (e.g. yeast, fungi and algae) microorganisms. Exemplary bacterial microorganisms include the genera *Escherichia, Bacillus, Klebsiella, Lactobacillus, Lactococcus,* and the like. Exemplary algae include the genus *Chlorella, Thraustochytriu, Schizochytrium, Crypthecodinium,* and the like. In some embodiments, the algae are heterotrophic algae.

Exemplary yeast and fungus include the genera of *Aspergillus, Candida, Pichia, (Hansenula), Phanerochaete, Kloeckera (Hanseniaspora), Kluyveromyces, Rhodotorula, Torulopsis, Zygosaccharomyces, Yarrowia,* and *Saccharomyces*.

In some embodiments, the microorganisms include *Escherichia coli, Klebsiella oxytoca, Zymomonas mobilis, Clostridium thermocellum, Pichia pastoris, Pichia stipites, Candida albicans, Saccharomyces cerevisiae, Phanerochaete chrysosporium Schizosaccharomyces pombe,* and/or *Yarrowia lipolytica*.

In some embodiments, the microorganism to be propagated includes genetically modified yeast such as genetically modified *Saccharomyces cerevisiae*. According to one embodiment, the yeast is a strain of *Saccharomyces cerevisiae* yeast. In some embodiments, the yeast is a strain of *Saccharomyces cerevisiae* capable of converting, namely fermenting, glucose, xylose, arabinose or a combination thereof. In other embodiments, the yeast is a genetically modified strain of *Saccharomyces cerevisiae* yeast capable of growing on lignocellulosic hydrolysate or treated lignocellulosic hydrolysate. Lignocellulosic fermentation utilizes plant dry matter (lignocellulose) which is composed of cellulose, hemicellulose, and lignin. In still other embodiments, the yeast strain is a non-genetically modified strain (e.g. *Saccharomyces cerevisiae*).

Suitable yeasts include any of a variety of commercially available yeasts, such as commercial strains of *Saccharomyces cerevisiae* available under the trade names, e.g., Ethanol Red® from LeSaffre or TransFerm® from Mascoma Corporation. Exemplary yeast strains can ferment xylose and/or glucose into an alcohol such as ethanol. For example, a useful strain of yeast includes *Saccharomyces cerevisiae* yeast altered to convert (i.e., ferment) xylose and glucose to ethanol (i.e., a genetically modified yeast derived from an organism as described in U.S. Pat. No. 7,622,284). As another example, a useful strain of yeast includes *Sac-*

*charomyces cerevisiae* yeast altered (i.e., genetically modified) to convert (i.e., ferment) xylose, arabinose, and glucose to ethanol. In embodiments, the first cell mass of the microorganism is added to a propagation medium having polysaccharides that are saccharified and used for propagation. In embodiments, the first cell mass of the microorganism is from about 0.001 to 0.1% (wt) of solids of the stillage composition. In other embodiments, the first cell mass of the microorganism are added from about 0.005% to 0.1% (wt), from 0.01% to 0.05% (wt), from 0.05% to 0.1% (wt), from 0001% to 0.005% (wt) of solids of the stillage composition. Commercially available yeasts have average cell weights in the range of about $3\text{-}4\times10^{-11}$ grams. Accordingly, for a propagation medium having about 15% (wt) solids (150 mg/g), microorganism can be added in a range of about $5\times10^4$ CFU to about $5\times10^6$ CFU per gram of propagation medium.

Propagating the microorganism can begin when the microorganism is present in the propagation medium and desired conditions are present. Conditions to consider for propagation of a microorganism include, e.g., amount of stillage composition, enzyme(s), microorganism, pH, time for growth of the microorganism, stir speed (if stirring is present), exposure to oxygen, temperature, and the like.

The cell mass can be propagated, depending on conditions, for a time to produce a desired cell mass. Typically, the desired cell mass is a size sufficient to ferment sugar into an alcohol (e.g., ethanol) within an economically desirable time. Exemplary time periods include from 12-80 hours, 12-48 hours, 12-24 hours, 24-48 hours, 48-60 hours, 60-80 hours, or 48-80 hours. In exemplary embodiments, the desired (e.g., second or final) cell mass of the microorganism (e.g. yeast) is present in an amount in the range from 10 to 1000 times the initial or first cell mass of the microorganisms, 200-1000 times, 300-800, 500-1000 times, 100-1000 times. In other embodiments the second or final cell mass of the microorganism (e.g. yeast) is present in an amount in the range from 10-35 times the initial or first cell mass of the microorganisms, from 20-30 times, 15-25 times, or from 15-35 times the initial or first cell mass of the microorganisms. In embodiments, the second cell mass of the organism is grown within a time period in the range of from 8-80, from 12-48 hours, from 12-24 hours or from 12-60 hours, wherein the time period begins when the first cell mass of the microorganism is combined with the propagation medium to propagate the first cell mass of the microorganism.

The pH of the propagation medium can be at a pH that helps reproduce (propagate) and generate a desired population of microorganism (e.g., ethanologen) within a desired amount of time. In some embodiments, the pH is between 4 and 8, between 5 and 7, or between 4.5 and 6. Techniques for adjusting and maintaining pH of a propagation medium for propagating microorganisms such as an ethanologen are well known and include, e.g., adding one or more acidic materials and/or adding one or more basic materials.

The temperature of the propagation medium can be at a temperature that helps reproduce (propagate) and generate a desired population of microorganism (e.g., ethanologen) within a desired amount of time. In some embodiments, the temperature is in the range of from 15° C. to 50° C., from 20° C. to 40° C., from 25° C. to 40° C., from 25° C. to 37° C., or from 20° C. to 37° C., 20° C. to 30° C., 30° C. to 50° C., or 50° C. to 60° C.

In embodiments, the second or final cell mass of the microorganism is present in an amount in the range of from 10-30 times the initial or first cell mass within a time period in the range of from 12 to 48 hours, at a pH from about 4-6 and at a temperature from 25-37° C.

Propagation of a microorganism can be performed according to a continuous process, fed-batch process, a batch process, or combinations thereof. In embodiments, a batch process is desirable as it is relatively easier to manage and control as compared to a continuous or fed-batch process.

In some embodiments, the propagation medium is aerated for at least a portion of the propagation process to promote aerobic respiration and, therefore, reproduction of the microorganism instead of, e.g., anaerobic fermentation production of ethanol. In some embodiments, if sufficient aeration is not provided to the propagation medium, the process can switch to an anaerobic pathway and promote fermentation so as to produce alcohol to an undue degree. In embodiments, propagation is aerated at 0.025 to 10 vessel volumes of air per minute, from 0.025 to 0.05, 0.05 to 0.1, 0.1 to 1.0, 1 to 5, or 5 to 10 vessel volumes per minute.

In an embodiment, a biorefinery having a corn-grain ethanol process is co-located with a cellulosic ethanol process. Such processes can be physically located relatively near each other such as within several hundred yards such that piping and like can be easily installed between the two processes. In one embodiment is a system of propagation. Stillage composition is provided to a propagation system from a corn starch ethanol process. In some embodiments, the stillage composition is a stillage component from a dry grind corn starch ethanol process. Propagation system can include at least one vessel in fluid communication with the stillage composition so that the stillage composition can be added to the at least one vessel.

Treatment of the stillage composition can be performed with one or more enzymes in one or more treatment stages. In one mode of practice, a single enzyme in a single treatment stage is performed. In another mode of practice, two or more enzymes in a single treatment stage is performed. In another mode of practice, two treatment stages are performed, each treatment stage using a single enzyme. In yet another mode of practice, two treatment stages are performed, one treatment stage using a single enzyme, and the other treatment stage using two or more enzymes. In yet another mode of practice, two treatment stages are performed, each treatment stage using two or more enzymes.

In other embodiments, a single stage enzyme treatment is performed. The single stage treatment can be performed under conditions resulting in a desired conversion of polysaccharides to monosaccharides, such as in the higher or lower temperature ranges as described herein.

In some embodiments, a propagation medium formed from a stillage composition, and at least one alpha-amylase are added to the at least one vessel of the propagation system and held at a temperature in the range from 65° C. to 80° C. (e.g., about 70° C.) for a time period in the range from 1 to 3 hours. During this time period, the alpha-amylase can facilitate converting at least a portion of any residual polysaccharides to one or more oligosaccharides. Also, this temperature holding period can help pasteurize at least a portion of any bacterial contamination that may be present. Advantageously, including pasteurization helps the yeast propagate sooner and with less competition for glucose. After this, the propagation medium is cooled for a period of time sufficient for the medium to reach a temperature safe for addition of a first cell mass of microorganisms.

In some embodiments, the contents of the at least one vessel can be cooled to a temperature in the range from 20° C. to 40° C. (e.g., about 31° C.). During and/or after cooling, gluco-amylase can be added to facilitate converting one or more oligosaccharides into one or more monosaccharides so that the first cell mass of the microorganism can utilize the monosaccharides to propagate into the second cell mass of the microorganism. For example, in some embodiments, residual starch in the stillage composition is converted into glucose. In some embodiments, a propagation vessel can be coupled to an aerator to facilitate propagation. A propagation medium can be held at a temperature in the range from 20° C. to 40° C. (e.g., about 31° C.) for a time period of from 10-20 hours (e.g., about 15-16 hours).

In other embodiments, a single stage enzyme treatment is performed. The single stage treatment can be performed under conditions resulting in a desired conversion of polysaccharides to monosaccharides, such as in the higher or lower temperature ranges as described herein. In some embodiments, propagation is performed in one or more stages. In one example, yeast propagated in a propagation system having at least two stages. In a first stage, a yeast culture is grown into an initial yeast inoculum. In the first propagation stage, the initial yeast inoculum is introduced into a vessel and diluted (e.g. by 250×). According to exemplary embodiments, the temperature may be maintained in a range of about 26 to 37 degrees Celsius and the pH in a range of about 3.5 to 6.5 for a time of at least 24 hours. For example, yeast can be grown in the first propagation stage under conditions including a temperature of about 30 degrees Celsius and a pH of about 5.5 for about 24 hours.

In the second propagation stage, the yeast inoculum from the first propagation stage is diluted (e.g. by 10×), typically after being transferred to another vessel and a portion of stillage composition is supplied. According to exemplary embodiments, the temperature may be maintained in a range of about 26 to 37 degrees Celsius and the pH in a range of about 3.5 to 6.5 for a time of at least 24 hours. For example, yeast can be grown in the second propagation stage under conditions comprising a temperature of about 30 Celsius and a pH of about 4.5 to about 5.5 for about 24 hours.

According to an embodiment, the yeast cell mass will grow by about 200 to 500 fold in the first stage and about 20 to 40 fold in the second stage.

In embodiments, saccharification of the stillage composition is performed separately, and before, propagation. In other embodiments, the stillage composition is saccharified to break down polysaccharides at the same time the microorganisms are grown on the stillage composition. Simultaneous saccharifying and propagating can be conducted using the ingredients (yeast, enzymes, stillage composition) and conditions described above for saccharifying and propagating.

In an embodiment, saccharification and propagation is conducted at a temperature of about 25° C. to about 40° C. or about 30° C. to about 35° C. In an embodiment, during simultaneous saccharification and propagation the temperature is decreased from about 40° C. to about 25° C. or from about 35° C. to about 30° C.

In some embodiments, the yeast is propagated simultaneously with saccharification on a stillage composition. In other embodiments, the yeast is propagated simultaneously with saccharification on whole stillage, syrup or both. In still other embodiments, yeast is propagated simultaneously with saccharification on whole stillage using amylases. In other embodiments, the yeast is propagated simultaneously with saccharification on whole stillage using cellulases, amylases, or a combination thereof.

The resultant microorganisms that are propagated by the described methods are used in fermentation processes to convert sugars into a desired bioproduct such as ethanol. In embodiments, the microorganisms propagated can be "conditioned" or adapted for fermentation by exposing the microorganisms to medium that they are likely to encounter during fermentation.

The Examples below further illustrate embodiments of the invention.

EXAMPLE 1

Samples of whole stillage and syrup were saccharified resulting in glucose or xylose. A whole stillage sample with 15% total solids (=100% whole stillage) and a syrup sample with 35.5% total solids (=100% syrup) were diluted with reverse osmosis water to 50% whole stillage and 50% syrup, or left undiluted with water (100% whole stillage, 100% syrup), and the pH adjusted to 5.0 using 30% ammonium hydroxide.

50 gm of the various samples were loaded into 125 mL baffled Erlenmeyer flasks. LACTROL™ antibiotic (commercially available from PhibroChem) was added to control bacterial contamination at 2 ppm of the total propagation medium and the flasks later dosed with Enzyme Mixture A (an enzyme cocktail of cellulases and hemicellulases; EM-A), Enzyme Mixture B (an enzyme cocktail of alpha amylases and glucoamylases; EM-B), or both enzymes at 1× or 5× doses (see dosing definitions below).

A 1× Enzyme Mixture A is equal to 0.04 gms/gm solids in stillage stream. A 1× Enzyme Mixture B, is equal to 0.0007 gm/gm solids in stillage stream. Enzyme mixture A used at 0.04 gms/gm solids is sufficient to convert 45% (wt) of the polysaccharides in the stillage composition to monosaccharides. Details of EM-B enzymatic mixture and activity are described in U.S. Pat. No. 7,842,484.

Figure 2A:
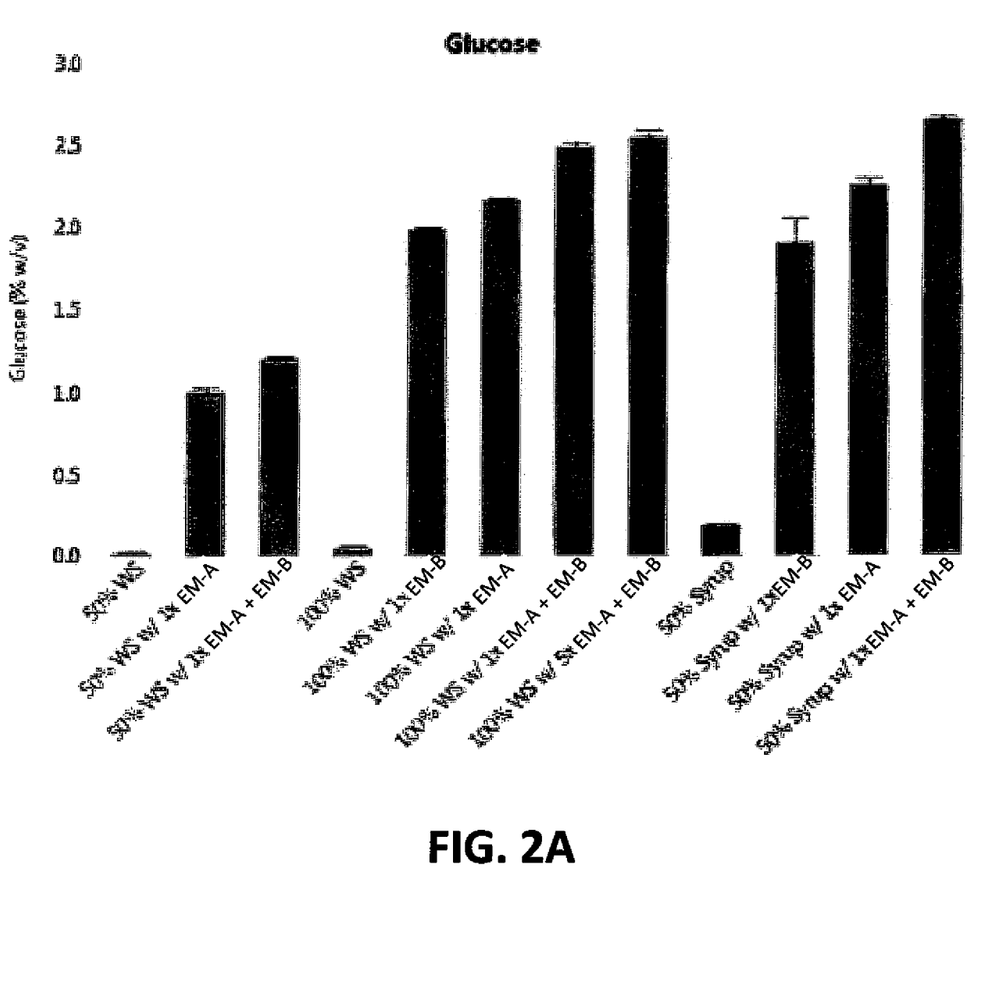
FIG. 2A shows a bar graph of glucose produced according to conditions in Example 1.
Figure 2B:
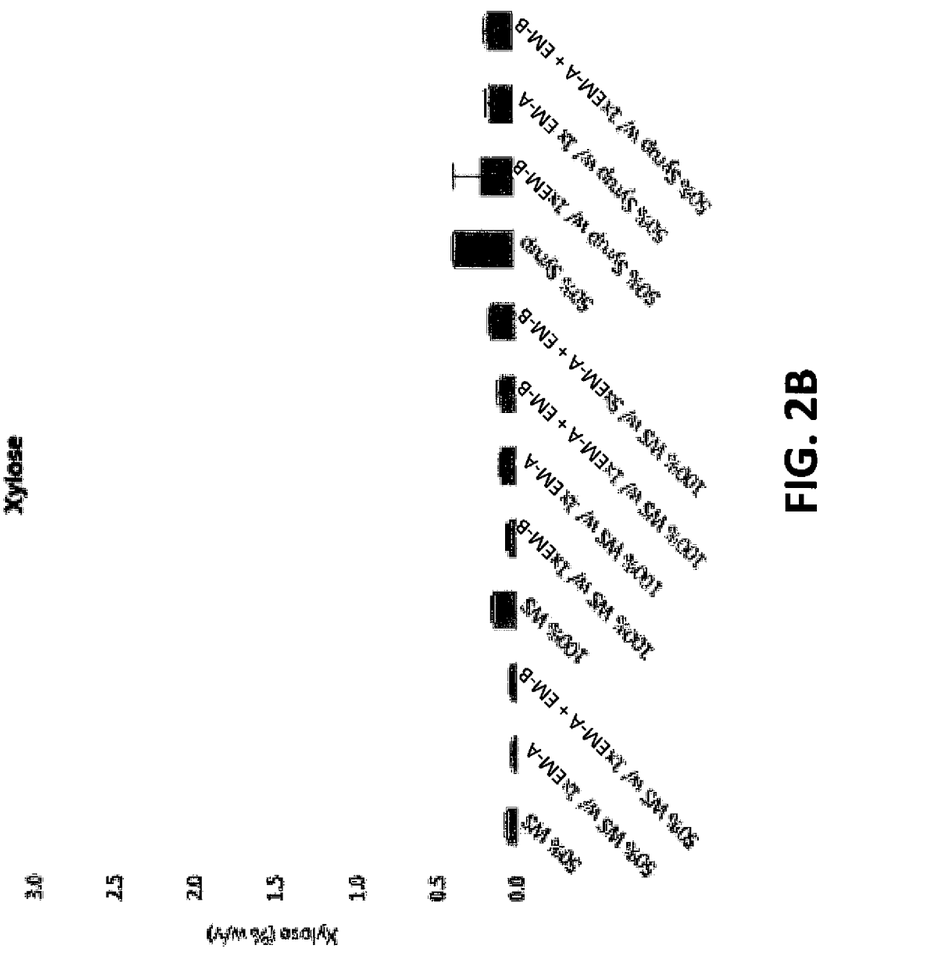
FIG. 2B shows a bar graph of xylose produced according to conditions in Example 1.

The Erlenmeyer flasks were closed with rubber stoppers and the samples incubated at 55° C. and shaken at 150 RPM for 24 hours. Samples were analyzed for glucose or xylose after 24 hours of saccharification and results are shown in FIGS. 2A and 2B.

The results show that whole stillage is a better sugar source than syrup when the sugar release was normalized to solids. Less sugar was produced using only EM-B enzymes compared to EM-A or EM-A+EM-B.

EXAMPLE 2

This example evaluated whether saccharification (as conducted in Example 1) followed by propagation (separate saccharification and propagation) would yield better cell growth compared to simultaneously conducting saccharification and propagation (referenced here as SSP).

The samples used for separate saccharification and propagation were samples treated as in Example 1. SSP samples were simultaneously treated with enzymes (as described in Example 1 and shown in FIG. 3) and the addition of yeast.

Samples for both saccharified or SSP were pH adjusted to 5.5 using 30% ammonium hydroxide. LACTOSIDE 247™ antibiotic (commercially available from Lallemand Ethanol Technology Milwaukee, Wis.) was added to control bacterial contamination at 2 ppm of the total propagation medium. Flasks of the different samples were inoculated at 0.22 g/L by dried cell weight of a xylose-consuming active dry yeast. The flasks were incubated for 17 hours in an incubator set at 31.1° C. and shaken with a shaker set at the rate of about 150 RPM to aerate the flasks. Samples were removed after 17 hours and analyzed for cell growth as shown in FIG. 3.

Figure 3:
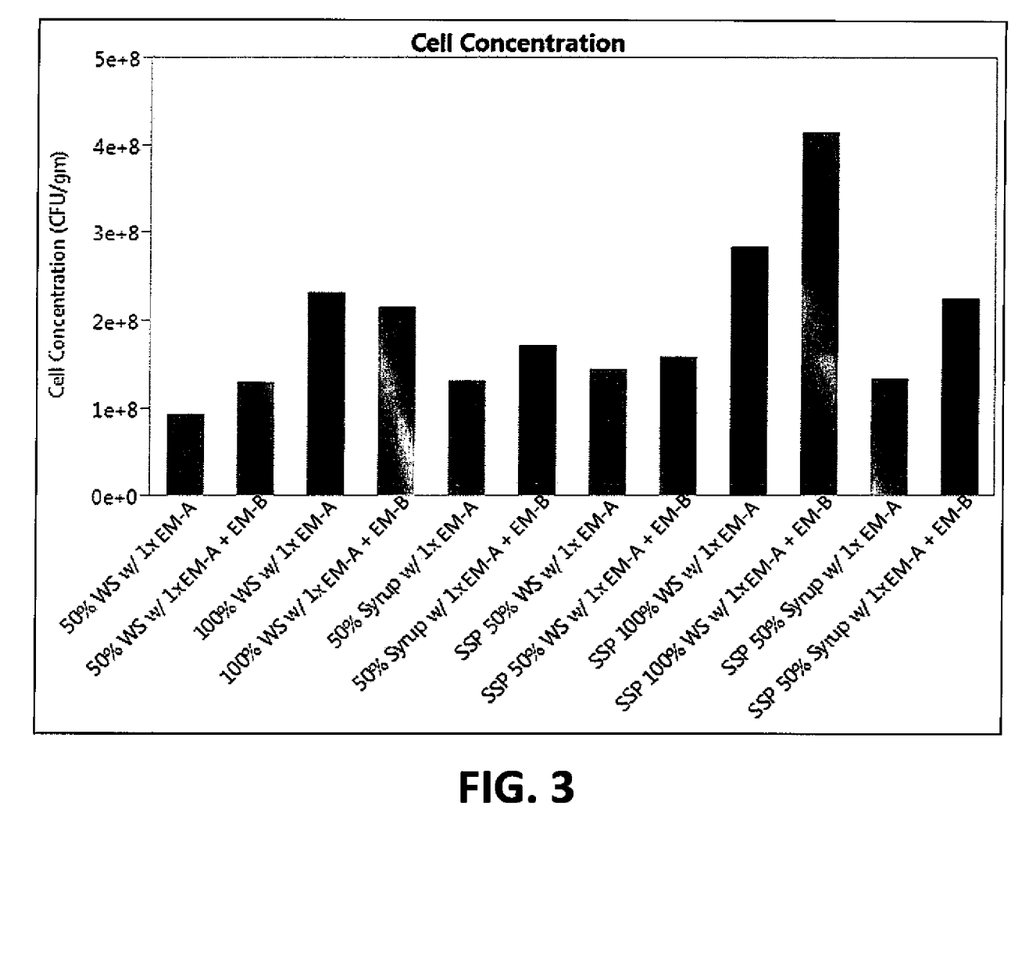
FIG. 3 shows a bar graph of propagated cells according to conditions in Example 2.

FIG. 3 shows that a higher cell concentration was obtained with whole stillage compared to syrup with similar solids content even with similar initial sugar levels. All the propagations reached at least $9 \times 10^7$ CFU/gm. A higher cell concentration was obtained with SSP than with separate saccharification followed by propagation. Commercially available yeasts have average cell weights in the range of about $3\text{-}4\times10^{-11}$ grams, and given the cell concentration in FIG. 3 being in the range of about 1 to about $5\times10^8$ colony forming units (CFUs) per g of medium (mL), the amount of yeast is in the range of about 3.5 mg to about 17.5 mg per g (mL) of medium.

The following are additional examples of the disclosure:

EXAMPLE 3

A method of propagating a microorganism for use in a lignocellulosic fermentation process, the method comprising: providing a propagation medium comprising: a stillage composition obtained from a starch-based fermentation process, the stillage composition comprising polysaccharides, wherein the majority of the polysaccharides in the propagation medium are from the stillage composition; an enzyme component comprising one or more enzymes selected from cellulases, amylases, and combinations thereof; converting the polysaccharides into one or more monosaccharides using the enzyme component; growing a first cell mass of the microorganism on the one or more monosaccharides from the stillage composition to form a second cell mass of the microorganism, wherein the second cell mass of the microorganism is greater than the first cell mass of the microorganism; and using the second cell mass in a lignocellulosic fermentation process.

EXAMPLE 4

The method of example 3 wherein at least 99% (wt) of the polysaccharides in the propagation medium are from the stillage composition.

EXAMPLE 5

The method of example 3 or 4 wherein the polysaccharides are present in an amount of about 2% (wt) or greater in the propagation medium.

EXAMPLE 6

The method of example 5 wherein the polysaccharides are present in an amount in the range of about 2% (wt) to about 10% (wt) in the propagation medium.

EXAMPLE 7

The method of any of the previous examples, wherein the stillage composition is whole stillage, syrup, or a combination thereof.

EXAMPLE 8

The method of any of the previous examples, wherein the stillage composition is a by-product of fermenting plant material.

EXAMPLE 9

The method of any of the previous examples, wherein the enzyme component ranges from 0.1 to about 10 units per gram of solids.

EXAMPLE 10

The method of any of the previous examples, wherein the enzyme component comprises cellulase, amylases and combinations thereof.

EXAMPLE 11

The method of example 10, wherein the enzyme component comprises cellulase.

EXAMPLE 12

The method of example 10 or 11, wherein the enzyme component comprises alpha-amylase, gluco-amylase or combinations thereof.

EXAMPLE 13

The method of any of the previous examples wherein the converting is at a pH in the range of 3 to 6 and at a temperature in the range of about 25° C. to 40° C. for a period of time in the range of 12 to 48 hours.

EXAMPLE 14

The method of any of the previous examples, wherein the converting and the growing steps are carried out partially or entirely simultaneously.

EXAMPLE 15

The method of any of the previous examples wherein the monosaccharide concentration during the growing is in the range of about 0.5% (wt) to about 3% (wt) of the propagation medium.

EXAMPLE 16

The method of any of the previous examples, wherein the first cell mass of the microorganism is about 0.001 weight percent to 0.1 weight percent of the solids content of the propagation medium.

EXAMPLE 17

The method of any of the previous examples, wherein the second cell mass of the microorganism is 10 to 1000 times the first cell mass of microorganisms.

EXAMPLE 18

The method of examples 17, wherein the second cell mass of the microorganism is 10-30 times the first cell mass.

EXAMPLE 19

The method of any of the previous examples, wherein the second cell mass is used for a lignocellulosic fermentation process.

EXAMPLE 20

The method of any of the previous examples, wherein the stillage composition is obtained following distillation of a bioproduct from a fermentation medium from a starch-based fermentation process.

EXAMPLE 21

The method of any of the previous examples, wherein the microorganism is yeast.

EXAMPLE 22

The method of example 21, wherein the yeast is a genetically modified yeast.

EXAMPLE 23

The method of example 21 or 22, wherein the yeast is *Saccharomyces cerevisiae.*

EXAMPLE 24

The method any one of examples 21-23, wherein the yeast is capable of growing on glucose, xylose, arabinose or a combination thereof.

EXAMPLE 25

A propagation medium consisting essentially of (i) a stillage composition that is whole stillage or syrup, (ii) one or more cellulases, amylases and combinations thereof that can convert the stillage composition into one or more monosaccharides, and a first cell mass of a microorganism, and optionally (iii) water.

EXAMPLE 26

A method for obtaining a stillage composition, using the stillage composition to propagate a microorganism, and then performing lignocellulosic fermentation, the method comprising: obtaining a stillage composition from a starch-based fermentation process that uses a plant material, wherein the stillage composition comprises polysaccharides; forming a propagation medium for propagating a microorganism, the medium comprising the stillage composition from the starch-based fermentation process, wherein polysaccharides in the propagation medium consist essentially of the polysaccharides from the stillage composition, and (ii) an enzyme component comprising one or more enzymes selected from cellulases, amylases, and combinations thereof, converting the polysaccharides into one or more monosaccharides using the enzyme component; propagating the microorganism in the propagation medium to generate a cell mass; and using the cell mass in a lignocellulosic fermentation process.

EXAMPLE 27

The method of example 26, wherein the stillage composition is obtained following distillation of a bioproduct from a fermentation medium from a starch-based fermentation process, and the second cell mass is used for a lignocellulosic fermentation process.

What is claimed is:

1. A method of propagating a microorganism for use in a lignocellulosic fermentation process, the method comprising:
   providing a propagation medium comprising:
      a stillage composition obtained from a starch-based fermentation process, the stillage composition comprising polysaccharides, wherein the majority of the polysaccharides in the propagation medium are from the stillage composition;
      an enzyme component comprising one or more enzymes selected from cellulases, amylases, and combinations thereof,;
   converting the polysaccharides into one or more monosaccharides using the enzyme component;
   growing a first cell mass of the microorganism on the one or more monosaccharides from the stillage composition to form a second cell mass of the microorganism, wherein the second cell mass of the microorganism is greater than the first cell mass of the microorganism; and
   using the second cell mass in a lignocellulosic fermentation process.

2. The method of claim 1 wherein at least 99% (wt) of the polysaccharides in the propagation medium are from the stillage composition.

3. The method of claim 1 wherein the polysaccharides are present in an amount of about 2% (wt) or greater in the propagation medium.

4. The method of claim 3 wherein the polysaccharides are present in an amount in the range of about 2% (wt) to about 10% (wt) in the propagation medium.

5. The method of claim 1, wherein the stillage composition is whole stillage, syrup, or a combination thereof.

6. The method of claim 1, wherein the enzyme component ranges from 0.1 to about 10 units per gram of solids.

7. The method of claim 1, wherein the enzyme component comprises cellulase.

8. The method of claim 1, wherein the enzyme component comprises alpha-amylase, gluco-amylase or combinations thereof.

9. The method of claim 1 wherein the converting is at a pH in the range of 3 to 6 and at a temperature in the range of about 25° C. to 40° C. for a period of time in the range of 12 to 48 hours.

10. The method of claim 1, wherein the converting and the growing steps are carried out partially or entirely simultaneously.

11. The method of claim 1, wherein the monosaccharide concentration during the growing is in the range of about 0.5% (wt) to about 3% (wt) of the propagation medium.

12. The method of claim 1, wherein the first cell mass of the microorganism is about 0.001 weight percent to 0.1 weight percent of the solids content of the propagation medium.

13. The method of claim 1, wherein the second cell mass of the microorganism is 10 to 1000 times the first cell mass of microorganisms.

14. The method of claim 13, wherein the second cell mass of the microorganism is 10-30 times the first cell mass.

15. The method of claim 1, wherein the stillage composition is obtained following distillation of a bioproduct from a fermentation medium from a starch-based fermentation process.

16. The method of claim 1, wherein the microorganism is yeast.

17. The method of claim 16, wherein the yeast is a genetically modified yeast.

18. The method of claim 16, wherein the yeast is *Saccharomyces cerevisiae.*

19. A method for obtaining a stillage composition, using the stillage composition to propagate a microorganism, and then performing lignocellulosic fermentation, the method comprising:
   obtaining a stillage composition from a starch-based fermentation process that uses a plant material, wherein the stillage composition comprises polysaccharides;
   forming a propagation medium for propagating a microorganism, the medium comprising the stillage composition from the starch-based fermentation process, wherein polysaccharides in the propagation medium consist essentially of the polysaccharides from the stillage composition, and (ii) an enzyme component comprising one or more enzymes selected from cellulases, amylases, and combinations thereof, converting the polysaccharides into one or more monosaccharides using the enzyme component;

propagating the microorganism in the propagation medium to generate a cell mass; and using the cell mass in a lignocellulosic fermentation process.

20. The method of claim 7, wherein the enzyme component comprises a mixture of cellulase, hemicellulose, alpha-amylase, and gluco-amylase.

\* \* \* \* \*